United States Patent [19]

Payne

[11] Patent Number: 5,651,965

[45] Date of Patent: Jul. 29, 1997

[54] *BACILLUS THURINGIENSIS* TOXINS AND GENES ACTIVE AGAINST NEMATODES

[75] Inventor: Jewel M. Payne, San Diego, Calif.

[73] Assignee: Mycogen Corporation, San Diego, Calif.

[21] Appl. No.: 310,197

[22] Filed: Sep. 21, 1994

Related U.S. Application Data

[62] Division of Ser. No. 92,155, Jul. 15, 1993, Pat. No. 5,350,577, which is a division of Ser. No. 918,345, Jul. 21, 1992, Pat. No. 5,270,448, which is a division of Ser. No. 558,738, Jul. 27, 1990, Pat. No. 5,151,363.

[51] Int. Cl.$^6$ .............................. A01N 63/00; C12N 5/04; C12N 1/20; C12N 1/15
[52] U.S. Cl. .................. 424/93.21; 424/93.2; 435/252.3; 435/252.31; 435/252.33; 435/252.34; 435/252.35; 435/254.11; 435/254.2; 435/254.21; 435/418; 435/419
[58] Field of Search .............................. 435/240.2, 240.4, 435/252.3, 252.31, 252.33, 252.34, 252.35, 254.11, 254.2, 254.21; 424/93.2, 93.21

[56] References Cited

PUBLICATIONS

Barton et al., Plant. Physiol., 85:1103–1109 (1987).
Prichard, R.K. et al. (1980) "The Problem of Anthelmintic Resistance in Nematodes" Australian Veterinary Journal 56:239–251.
Coles, G.C. (1986) "Anthelmintic Resistance in Sheep" Veterinary Clinics of North America: Food Animal Practice 2(2):423–432.
Bottjer, K.P., L.W. Bone, S.S. Gill (1985) "Nematoda: Susceptibility of the Egg to *Bacillus thuringiensis* Toxins" Experimental Parasitology 60:239–244.
Ignoffo, C.M., V.H. Dropkin (1977) "Deleterious Effects of the Thermostable Toxin of *Bacillus thuringiensis* on Species of Soil–Inhibiting, Myceliophagus, and Plant–Parasitic Nematodes" Journal of the Kansas Entomological Society 50(3):394–398.
Ciordia, H., W.E. Bizzell (1961) "A Preliminary Report on the Effects of *Bacillus thuringiensis* var. *thuringiensis* Berliner on the Development of the Free–Living Stages of Some Cattle Nematodes" Journal of Parisitology 47:41, abstract No. 86.

*Primary Examiner*—Nancy T. Vogel
*Attorney, Agent, or Firm*—Saliwanchik & Saliwanchik

[57] ABSTRACT

The invention concerns novel isolates of *Bacillus thuringiensis* (B.t.) which contain a toxin(s) which is active against nematodes. This B.t. toxin(s) or B.t. isolate(s) can be used to treat animals and plants hosting susceptible nematodes.

4 Claims, 1 Drawing Sheet

BACILLUS THURINGIENSIS TOXINS AND GENES ACTIVE AGAINST NEMATODES

CROSS-REFERENCE TO A RELATED APPLICATION

This application is a division of application Ser. No. 08/092,155, filed Jul. 15, 1993, now U.S. Pat. No. 5,350,522 which is a division of application Ser. No. 07/918,345, filed Jul. 21, 1992, now U.S. Pat. No. 5,270,448, which was a division of application Ser. No. 07/558,738, filed Jul. 27, 1990, now U.S. Pat. No. 5,151,363.

BACKGROUND OF THE INVENTION

Regular use of chemicals to control unwanted organisms can select for drug resistant strains. This has occurred in many species of economically important insects and has also occurred in nematodes of sheep, goats, and horses. The development of drug resistance necessitates a continuing search for new control agents having different modes of action.

In recent times, the accepted methodology for control of nematodes has centered around the drug benzimidazole and its congeners. The use of these drugs on a wide scale has led to many instances of resistance among nematode populations (Prichard, R. K. et al. [1980] "The problem of anthelmintic resistance in nematodes," Austr. Vet. J. 56:239–251; Coles, G. C. [1986] "Anthelmintic resistance in sheep," In *Veterinary Clinics of North America: Food Animal Practice*, Vol 2:423–432 [Herd, R. P., eds.] W. B. Saunders, New York). There are more than 100,000 described species of nematodes.

The bacterium *Bacillus thuringiensis* (B.t.) produces δ-endotoxin polypeptides that have been shown to have activity against a rapidly growing number of insect species. The earlier observations of toxicity only against lepidopteran insects have been expanded with descriptions of B.t. isolates with toxicity to dipteran and coleopteran insects. These toxins are deposited as crystalline inclusions within the organism. Many strains of B.t. produce crystalline inclusions with no demonstrated toxicity to any insect tested.

A small number of research articles have been published about the effects of δ-endotoxins from *B. thuringiensis* species on the viability of nematode eggs. Bottjer, Bone, and Gill (Experimental Parasitology 60:239–244, 1985) have reported that *B.t. kurstaki* and *B.t. israelensis* were toxic in vitro to eggs of the nematode *Trichostrongylus colubriformis*. In addition, 28 other B.t. strains were tested with widely variable toxicities. The most potent had $LD_{50}$ values in the nanogram range. Ignoffo and Dropkin (Ignoffo, C. M. and Dropkin, V. H. [1977] J. Kans. Entomol. Soc. 50:394–398) have reported that the thermostable toxin from *Bacillus thuringiensis* (beta exotoxin) was active against a free-living nematode, *Panagrellus redivivus* (Goodey); a plant-parasitic nematode, *Meloidogyne incognita* (Chitwood); and a fungus-feeding nematode, *Aphelenchus avena* (Bastien). Beta exotoxin is a generalized cytotoxic agent with little or no specificity. Also, H. Ciordia and W. E. Bizzell (Jour. of Parasitology 47:41 [abstract] 1961) gave a preliminary report on the effects of *B. thuringiensis* on some cattle nematodes.

At the present time there is a need to have more effective means to control the many nematodes that cause considerable damage to susceptible hosts. Advantageously, such effective means would employ biological agents.

BRIEF SUMMARY OF THE INVENTION

The subject invention concerns novel isolates of *Bacillus thuringiensis* that are active against nematodes. Test results for the nematode *Panagrellus redivivus* are disclosed. This nematode is commonly called the beer-mat nematode. It is a common free-living nematode that is relative easy to maintain in the laboratory. It is used as an indicator (model) of nematode activity.

The B.t. isolates of the invention can be grown and the δ-endotoxin that is produced recovered by standard procedures. The recovered toxin or the B.t. isolates can be formulated using standard procedures associated with the use of nematicidal products.

The novel B.t. isolates are named B.t. strain PS80JJ1, B.t. strain PS158D5, B.t. strain PS167P, B.t. strain PS169E, B.t. strain PS177F1, B.t. strain PS177G, B.t. strain PS204G4, and B.t. strain PS204G6.

Figure 1A:
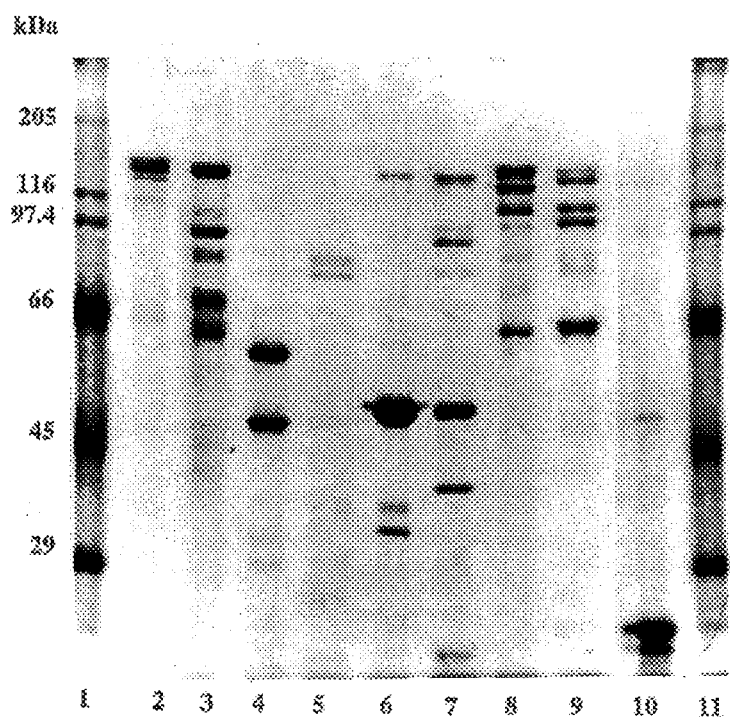
FIG. 1—Photograph of 9% SDS polyacrylamide gel electrophoresis showing alkali-soluble proteins of nematode active strains.
Figure 1B:
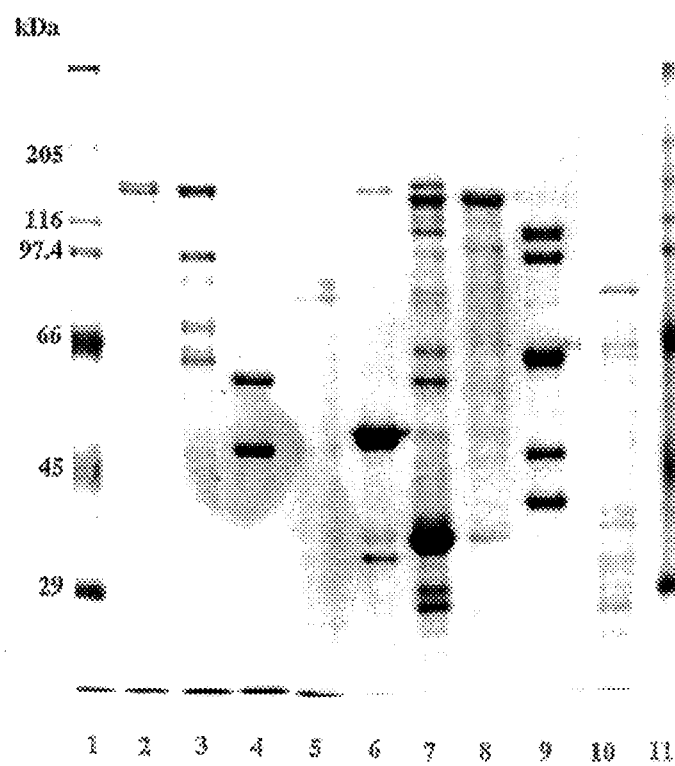

Gel A: Lane (1) Protein standard, (2) PS17, (3) PS33F2, (4) PS52A1, (5) PS63B, (6) PS69D1, (7) PS80JJ1, (8) PS177F1, (9) PS177G, (10) PS204G6, (11) Protein standard.

Gel B: Lane (1) Protein standard, (2) PS17, (3) PS33F2, (4) PS52A1, (5) PS63B, (6) PS69D1, (7) PS169E, (8) PS167P, (9) PS204G4, (10) PS158D5, (11) Protein standard.

DETAILED DISCLOSURE OF THE INVENTION

The novel B.t. isolates of the subject invention have been deposited in the permanent collection of the Agricultural Research Service Patent Culture Collection (NRRL), Northern Regional Research Center, 1915 North University Street, Peoria, Ill. 61604, USA. The accession numbers are as follows:

| Culture | Repository No. | Deposit Date |
| --- | --- | --- |
| B.t. strain PS80JJ1 | NRRL B-18679 | July 17, 1990 |
| B.t. strain PS158D5 | NRRL B-18680 | July 17, 1990 |
| B.t. strain PS167P | NRRL B-18681 | July 17, 1990 |
| B.t. strain PS169E | NRRL B-18682 | July 17, 1990 |
| B.t. strain PS177F1 | NRRL B-18683 | July 17, 1990 |
| B.t. strain PS177G | NRRL B-18684 | July 17, 1990 |
| B.t. strain PS204G4 | NRRL B-18685 | July 17, 1990 |
| B.t. strain PS204G6 | NRRL B-18686 | July 17, 1990 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

The novel B.t. isolates of the invention show activity against the tested nematode. It is expected that these isolates would be active against other nematodes as disclosed herein. The group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes wide-spread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris, Caenorhabditis, and Parascaris. Certain of these, such as Nematodirus, Cooperia, and Oesophagostomum, attack primarily the intestinal tract, while others, such as Dictyocaulus are found in the lungs. Still other parasites may be located in other tissues and organs of the body.

The toxins encoded by the novel B.t. genes of the invention are useful as nematocides for the control of soil nematodes and plant parasites selected from the genera Bursaphalenchus, Criconemella, Ditylenchus, Globodera, Helicotylenchus, Heterodera, Meloidogyne, Pratylenchus, Radolpholus, Rotelynchus, Panagrellus, or Tylenchus.

Alternatively, because some plant parasitic nematodes are obligate parasites, genes coding for nematocidal B.t. toxins can be engineered into plant cells to yield nematode-resistant plants. The methodology for engineering plant cells is well established (cf. Nester, E. W., Gordon, M. P., Amasino, R. M. and Yanofsky, M. F., Ann. Rev. Plant Physiol. 35:387–399, 1984).

The B.t. toxins of the invention can be administered orally in a unit dosage form such as a capsule, bolus or tablet, or as a liquid drench when used as an anthelmintic in mammals. The drench is normally a solution, suspension or dispersion of the active ingredient, usually in water, together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight, the capsules and boluses comprise the active ingredient admixed with a carrier vehicle such as starch, talc, magnesium stearate, or dicalcium phosphate.

Where it is desired to administer the toxin compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent, depending upon the factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or, optionally, fed separately. Alternatively, the antiparasitic compounds may be administered to animals parenterally, for example, by intraluminal, intramuscular, intratracheal, or subcutaneous injection, in which event the active ingredient is dissolved or dispersed in a liquid carrier vehicle. For parenteral administration, the active material is suitably admixed with an acceptable vehicle, preferably of the vegetable oil variety, such as peanut oil, cotton seed oil and the like. Other parenteral vehicles, such as organic preparations using solketal, glycerol, formal and aqueous parenteral formulations, are also used. The active compound or compounds are dissolved or suspended in the parenteral formulation for administration; such formulations generally contain from 0.005 to 5% by weight of the active compound.

When the toxins are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like.

In addition to having anthelminthic activity within the digestive tract of mammals, spores from nematicidal B.t. isolates will pass through the animals' digestive tract, germinate and multiply in the feces, and thereby provide additional control of nematode larva which hatch and multiply therein.

The gene(s) from the novel B.t. isolates of the subject invention can be introduced into microbes capable of occupying, surviving in, and proliferating in the phytosphere of plants according to the procedure of European Patent Application 0 200 344. Upon ingestion of such a plant by an animal hosting a nematode, the nematode-active toxin becomes available in the animal host to control the nematode infestation.

The toxin genes from the isolates of the subject invention can be introduced into a wide variety of microbial hosts. Expression of the toxin gene results, directly or indirectly, in the intracellular production and maintenance of the nematicide. With suitable hosts, e.g., Pseudomonas, the microbes can be applied to the situs of nematodes where they will proliferate and be ingested by the nematodes. The result is a control of the nematodes. Alternatively, the microbe hosting the toxin gene can be treated under conditions that prolong the activity of the toxin produced in the cell. The treated cell then can be applied to the environment of target pest(s). The resulting product retains the toxicity of the B.t. toxin.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the nematicide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are known and available for introducing the B.t. genes expressing the toxin into the microorganism host under conditions which allow for stable maintenance and expression of the gene. The transformants can be isolated in accordance with conventional ways, usually employing a selection technique, which allows for selection of the desired organism as against unmodified organisms or transferring organisms, when present. The transformants then can be tested for nematicidal activity.

Suitable host cells, where the nematicide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the B.t. gene into the host, availability of expression systems, efficiency of expression, stability of the nematicide in the host, and the presence of auxiliary genetic capabilities. Characteristics of interest for use as a nematicide microcapsule include protective qualities for the nematicide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economies, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., and the like. Specific organisms include *Pseudomonas aeruginosa, Pseudomonas fluorescens, Saccharomyces cerevisiae, Bacillus thuringiensis, Escherichia coli, Bacillus subtilis,* and the like.

The cell will usually be intact and be substantially in the proliferative form when treated, rather than in a spore form, although in some instances spores may be employed.

Treatment of the microbial cell, e.g., a microbe containing the B.t. toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the B.t. nematicidal gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The nematicide concentration will vary widely depending upon the nature of the particular formulation, particularly whether it is a concentrate or to be used directly. The nematicide will be present in at least 1% by weight and may be 100% by weight. The dry formulations will have from about 1–95% by weight of the nematicide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the nematodes, e.g., plants, soil or water, by spraying, dusting, sprinkling, or the like.

Following are examples which illustrate procedures, including the best mode, for practicing the invention. These examples should not be construed as limiting. All percentages are by weight and all solvent mixture proportions are by volume unless otherwise noted.

Example 1—Culturing B.t. Isolates

A subculture of B.t. isolate can be used to inoculate the following medium, a peptone, glucose, salts medium:

| | |
|---|---|
| Bacto Peptone | 7.5 g/l |
| Glucose | 1.0 g/l |
| KH$_2$PO$_4$ | 3.4 g/l |
| K$_2$HPO$_4$ | 4.35 g/l |
| Salt Solution | 5.0 ml/l |
| CaCl$_2$ Solution | 5.0 ml/l |
| Salts Solution (100 ml) | |
| MgSO$_4$.7H$_2$O | 2.46 g |
| MnSO$_4$.H$_2$O | 0.04 g |
| ZnSO$_4$.7H$_2$O | 0.28 g |
| FeSO$_4$.7H$_2$O | 0.40 g |
| CaCl$_2$ Solution (100 ml) | |
| CaCl$_2$.2H$_2$O | 3.66 g |
| pH 7.2 | |

The salts solution and CaCl$_2$ solution are filter-sterilized and added to the autoclaved and cooked broth at the time of inoculation. Flasks are incubated at 30 C on a rotary shaker at 200 rpm for 64 hr.

The above procedure can be readily scaled up to large fermentors by procedures well known in the art.

The B.t. spores and crystals, obtained in the above fermentation, can be isolated by procedures well known in the art. A frequently-used procedure is to subject the harvested fermentation broth to separation techniques, e.g., centrifugation.

Example 2—Activity of *Bacillus thuringiensis* Isolates Against *Panagrellus redivivus*

Worms are collected in a tube and allowed to settle for about 15 minutes, and the water is decanted and replaced with fresh water three or four times until the water remains clear. 250 µl rinsed nematodes (20–30 worms), and 100 µl of a spore/crystal suspension are added to 650 µl water in each well of tray. Nematodes are counted and the numbers recorded. After four days, the live worms are counted and percent mortality is calculated.

| Bioassay Results: Prior art (U.S.S.N. 084,653, filed August 12, 1987) | |
|---|---|
| B.t. strain No. | Mortality |
| PS17 | 90% |
| PS33F2 | 30% |
| PS52A1 | 100% |
| PS63B | 92% |
| PS69D1 | 100% |
| Novel Bt. strain No. | |
| PS80JJ1 | 99% |
| PS158D5 | 99% |
| PS167P | 96% |
| PS169E | 100% |
| PS177F1 | 96% |
| PS177G | 100% |
| PS204G4 | 100% |
| PS204G6 | 100% |
| Control | 0% |

The following table shows the molecular mass of the alkali-soluble proteins in each novel nematode-active strain, as compared to prior art B.t. strains.

| Prior Art Nematode-Active Strains | |
|---|---|
| B.t. Strain | Approximate Molecular Mass of Proteins(kDa) |
| PS17 | 155, 145, 135 |
| PS33F2 | 140, 94, 86, 68, 65, 62 |
| PS52A1 | 57, 45 |
| PS63B | 84, 82, 78 |
| PS69D1 | 135, 46, 32 |

| New Nematode-Active Strains | |
|---|---|
| Novel B.t. Strain | Approximate Molecular Mass of Proteins (kDa) |
| PS80JJ1 | 130, 90, 47, 37 |
| PS158D5 | 80 |
| PS167P | 120 |
| PS169E | 150, 128, 33 |
| PS177F1 | 140, 116, 103, 62 |
| PS177G | 135, 125, 107, 98, 62 |
| PS204G4 | 105, 98, 90, 60, 44, 37 |
| PS204G6 | 23, 21 |

I claim:

1. A microbe capable of occupying, surviving in, and proliferating in the phytosphere of plants wherein said microbe contains a *Bacillus thuringiensis* toxin-encoding gene derived from a *Bacillus thuringiensis* isolate selected from the group consisting of *Bacillus thuringiensis* strain PS80JJ1, *Bacillus thuringiensis* strain PS158D5, *Bacillus thuringiensis* strain PS167P, *Bacillus thuringiensis* strain PS169E, *Bacillus thuringiensis* strain PS177F1, *Bacillus thuringiensis* strain PS177G, *Bacillus thuringiensis* strain PS204G4, and *Bacillus thuringiensis* strain PS204G6.

2. A process for controlling nematodes comprising contacting said nematodes with a host transformed to express a *Bacillus thuringiensis* toxin gene derived from a *Bacillus thuringiensis* isolate selected from the group consisting of PS80JJ1, PS158D5, PS167P, PS169E, PS177F1, PS177G, PS204G4, and PS204G6, wherein a toxin encoded by said toxin gene is produced, and wherein said transformed host is a microbe or plant cell.

3. The process, according to claim 2, wherein said toxin is active against nematodes of the genera selected from the group consisting of Bursaphalenchus, Criconemella, Ditylenchus, Globodera, Helicotylenchus, Heterodera, Meloidogyne, Pratylenchus, Radolpholus, Rotelynchus, Panagrellus and Tylenchus.

4. A plant cell transformed to express a *Bacillus thuringiensis* toxin gene derived from a *Bacillus thuringiensis* isolate selected from the group consisting of PS80JJ1, PS158D5, PS167P, PS169E, PS177F1, PS177G, PS204G4, and PS204G6.

* * * * *

UNITED STATES PATENT AND TRADEMARK OFFICE
CERTIFICATE OF CORRECTION

PATENT NO.   :   5,651,965

DATED        :   July 29, 1997

INVENTOR(S)  :   Jewel M. Payne

It is certified that error appears in the above-identified patent and that said Letters Patent is hereby corrected as shown below:

Column 1, line 7: "U.S. Pat. No. 5,350,522" should read — U.S. Pat. No. 5,350,577—

Column 6, line 13: "economies" should read —economics—

Signed and Sealed this

Eighteenth Day of November 1997

*Attest:*

BRUCE LEHMAN

*Attesting Officer*     *Commissioner of Patents and Trademarks*